United States Patent [19]

Elliott

[11] Patent Number: 5,539,386

[45] Date of Patent: Jul. 23, 1996

[54] SENSOR FOR DETECTING AIR/LIQUID TRANSITIONS IN A TRANSPARENT TUBING

[75] Inventor: Robert C. Elliott, St. Louis, Mo.

[73] Assignee: J-KEM Electronics, Inc., Chesterfield, Mo.

[21] Appl. No.: 206,972

[22] Filed: Mar. 7, 1994

[51] Int. Cl.⁶ .................................................. G08B 17/103
[52] U.S. Cl. ........................ 340/632; 340/619; 250/573; 128/DIG. 13
[58] Field of Search .................................... 340/605, 619, 340/627, 632; 250/573, 577; 128/632, 633, 766, DIG. 12, DIG. 13; 604/250, 258; 93/293

[56] References Cited

U.S. PATENT DOCUMENTS

| | | | |
|---|---|---|---|
| 4,314,484 | 2/1982 | Bowman | 73/861 |
| 4,366,384 | 12/1982 | Jensen | 250/575 |
| 4,367,736 | 1/1983 | Gupton et al. | 340/632 |
| 4,487,601 | 12/1984 | Lindemann | 604/122 |
| 4,490,140 | 12/1984 | Carr et al. | 604/65 |
| 4,498,901 | 2/1985 | Finch | 604/65 |
| 4,565,500 | 1/1986 | Jeensalute et al. | 340/632 |
| 4,631,529 | 12/1986 | Zeitz | 340/619 |
| 4,857,050 | 8/1989 | Lentz et al. | 128/DIG. 13 |
| 4,857,894 | 8/1989 | Dahl | 340/619 |
| 4,884,065 | 11/1989 | Crouse et al. | 340/619 |
| 4,931,774 | 6/1990 | Bachman | 250/573 |
| 4,984,462 | 1/1991 | Hass, Jr. et al. | 73/293 |
| 5,073,720 | 12/1991 | Brown | 250/577 |
| 5,267,978 | 12/1993 | Dirr, Jr. | 604/246 |
| 5,274,245 | 12/1993 | Lee | 250/577 |

Primary Examiner—John K. Peng
Assistant Examiner—Daniel J. Wu
Attorney, Agent, or Firm—Senniger, Powers, Leavitt & Roedel

[57] ABSTRACT

A non-intrusive optical transmission liquid monitoring system that detects bubbles in a transparent liquid flowing through a transparent tubing. The system dynamically compensates for changes in optical transmission efficiency of the monitored liquid and distinguishes between the transition from liquid to air and air to liquid. A system comprising a light transmitter and a light sensitive receiver secured on opposite sides of a transparent tubing. The output of the receiver is fed into a self-referencing and drift compensation circuit. The integrated output is connected to circuitry sensitive to a change in the integrated output and triggers one of two possible alarms to indicate a detected transition from liquid to air, or air to liquid.

20 Claims, 4 Drawing Sheets

SENSOR FOR DETECTING AIR/LIQUID TRANSITIONS IN A TRANSPARENT TUBING

BACKGROUND

The present invention relates to the detection of bubbles or air in transparent tubing and, in particular, a sensor for detecting both air-liquid and liquid-air transition.

Bubbles or air pockets in transparent tubing result when liquid passing through the tubing runs out or a break in the tubing causes the introduction of air into the tubing system. Many modern laboratory operations require liquids to be pumped or passed through tubing connecting a solvent reservoir to an instrument or other operation. Pumping air through many instruments or introducing air in certain reactions can cause damage to instrumentation or in some cases create a significant safety hazard. In these situations, it is very important that tubing transporting the solvent be monitored for the presence of air just before the solvent enters an instrument or is added to the operation, such as a chemical reaction, so that action can be taken to prevent the introduction of the air.

A typical setup to monitor for air in solvent lines involves placing an energy source on one side of the tubing carrying the solvent and a receiver sensitive to the energy emitted by the energy source on the other side. For example, see U.S. Pat. Nos. 4,314,484 and 4,487,601, the entire disclosures of which are incorporated herein by reference. One common energy source that can be used as an example is a light emitting diode and its appropriate energy receiver is a photo transistor. Such a bubble detector works on the theory that when liquid is present in the tubing the photo detector produces a set output signal, the level of which can be measured to establish a "liquid present" output level. A reference voltage (or current) is then set which is slightly offset from the "liquid present" voltage and the two voltages are continuously compared. If a bubble develops in the tubing and passes between the light emitting diode and the photo detector, the output voltage of the photo detector changes causing it to fall below (or above) the reference voltage, thus signaling the presence of air.

This prior art detection approach has three principle disadvantages. First, it requires that the reference voltage be adjusted, usually manually, every time any part of the system that affects the output of the photo detector is changed. The output of the photo detector is affected by many properties such as the clarity of the liquid and the material of which the tubing is made including its transmittivity, wall thickness, and diameter. Also, other factors such as alignment of the transmitter/receiver pair and their relative efficiencies affect the output voltage of the photo detector. This heavy dependence on the system configuration requires that the reference voltage of the bubble detector be adjusted for each use.

A second disadvantage is that the prior art detection approach does not compensate for slow drift of the "liquid present" signal level. For many operations the liquid monitored in the tubing changes over the course of time, such as with gradient column chromatography where the starting solvent can be water but changes to acetonitrile over a certain time period, typically 30 minutes. Changing the solvent monitored in the tubing causes a change in the level of the "liquid present" voltage. If the change is significant enough the "liquid present" voltage can cross the reference voltage causing a false indication that air is present.

The third disadvantage of the prior art detection approach is that the difference between the output voltage from the photo detector when liquid is present and when air is present can be very small. This situation requires that the reference voltage be set very close to the "liquid present" voltage, close enough that even normal amounts of electrical noise can cause false detection of air.

An additional disadvantage is present in the design of some bubble detection devices, namely that they only detect the transition from liquid to air and not the transition from air to liquid. This is important for applications that do not turn off equipment when air is detected, but rather open a valve to purge air from the system. These applications require information not only that air is present to initiate the purge operation, but also that the transition from air to liquid has occurred to indicate the purge is complete.

SUMMARY OF THE INVENTION

Among the objects of the invention is the provision of a bubble detection apparatus which detects air in transparent tubing by attaching a photo transmitter and photo detector on opposite sides of the tubing and monitors for change in light transmission; the provision of a bubble detector which is insensitive to the absolute output voltage of the photo detector and automatically references to any detector output voltage between the limits of the positive and negative supplies; the provision of a bubble detector providing alarm output which is unresponsive to gradual changes in the photo detector's output level but is responsive to rapid changes; the provision of a bubble detection apparatus that produces separate signals for detected transitions from liquid to air and air to liquid; the provision of a bubble detection device which may be used with transparent tubing of varying diameters; the provision of such a device that automatically references to the output signal level of the photo detector and allows for gradual change of the reference level to compensate for drift in the photo detectors output signal without triggering the bubble detection alarm; the provision of such a device that is insensitive to the absolute output voltage of the photo detector, but responsive only to change in the photo detectors output; and the provision of such a device with two output lines, one that is activated when the transition from liquid to air is detected and the other when the transition from air to liquid is detected.

In one form, the invention comprises an apparatus for sensing transitions from liquid to gas or from gas to liquid in a tubing through which the liquid and the gas are flowing. The apparatus includes a transmitter, a receiver, and a detecting circuit. The transmitter is adapted to be adjacent the tubing and generates energy which propagates through the tubing and through the liquid and gas flowing through the tubing. The receiver is associated with the transmitter for detecting the energy transmitted through the liquid and gas flowing through the tubing. The receiver generates a detected signal representative of the transmitted energy. The detecting circuit detects a change in magnitude of the modified detected signal and generates a first alarm signal when the detected signal increases in magnitude and a generates a second alarm signal when the modified detected signal decreases in magnitude. The first alarm signal is representative of one of either a transition from liquid to gas or a transition from gas to liquid and the second alarm signal is representative of the other transition.

Other objects and features will be in part apparent and in part pointed out hereinafter.

BRIEF DESCRIPTION OF THE DRAWINGS

Corresponding reference characters indicate corresponding parts throughout the drawings.

DETAILED DESCRIPTION OF THE PREFERRED EMBODIMENT

Figure 1:
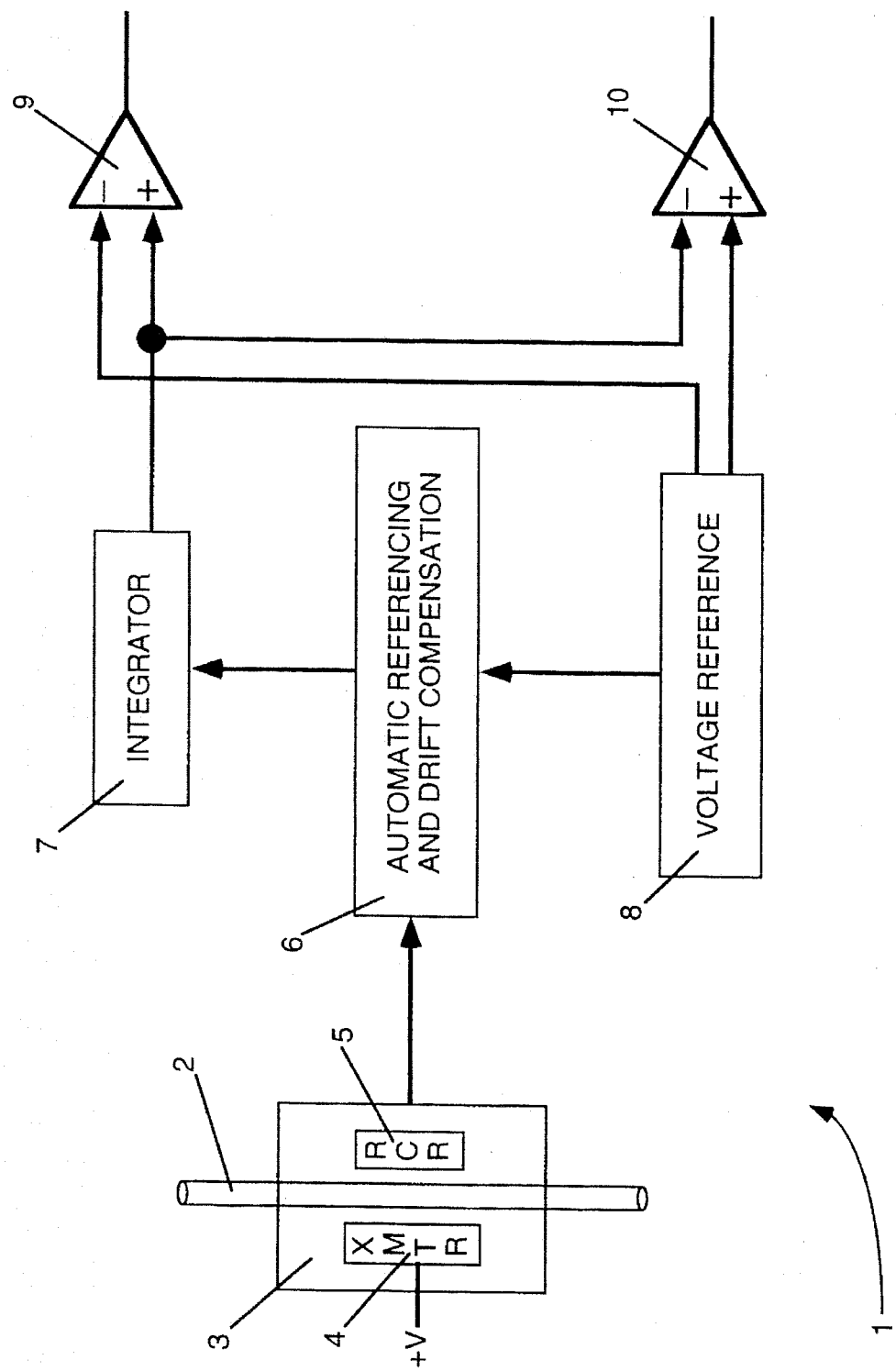
FIG. 1 is a block diagram of a system according to the invention for detecting air and liquid in transparent tubing with automatic referencing to the detectors output signal and drift compensation.

FIG. 1 illustrates a block diagram of an apparatus 1 according to the invention for detecting a transition from liquid to air (or other gas mixed with the liquid) and air (gas) to liquid in transparent tubing 2. Apparatus 1 has a detection head 3 consisting of a photo transmitter 4 such as a light emitting diode and a photo detector 5 such as a photo sensitive NPN transistor secured to opposite sides of the tubing 2. Light from the photo transmitter 4 travels through the tubing 2 and is received by the photo detector 5 which produces a proportionate output signal which in turn is feed to the referencing and drift compensation circuit 6.

In particular, when the proportionate output signal increases, such an increase suggests a transition from gas to liquid. This is because the tube filled with clear liquid transmits more light than the tube filled with gas so that the receiver receives more light after the transition and generates a first output signal having a proportionately higher output. Similarly, when the proportionate output signal decreases, such a decrease suggests a transition from liquid to gas. This is because gas transmits less light to the photo detector than liquid so that the receiver receives less light after the transition and generates a second output signal having a proportionately lower output.

Referencing and drift compensation circuit 6 performs three functions. First, circuit 6 shifts the relative output voltage sensed from receiver 5 to a known voltage level. Second, circuit 6 compensates and references for slow changes in the output signal of receiver 5. Third, circuit 6 supplies a positive going signal when a transition from liquid to air occurs and a negative going signal when a transition from air to liquid occurs.

The output of compensation and referencing circuit 6 is applied to an integrator 7 which integrates the output of 6 in either a positive or negative direction. If the time-voltage product of integrator 7 overtakes the reference voltage of amplifier 9 in a positive going direction, the output voltage of amplifier 9 rises providing a first alarm signal indicating a transition from liquid to air was detected by detector head 3. The positive going signal produced by amplifier 9 is the alarm signal that a liquid to air transition was detected in the solvent stream in delivery tube 2. If the time-voltage product of integrator 7 overtakes the reference voltage of amplifier 10 in a negative going direction, the output voltage of amplifier 10 rises providing a second alarm signal indicating a transition from air to liquid was detected by detector head 3. The positive going signal produced by amplifier 10 is the alarm signal that an air to liquid transition was detected in the solvent stream in delivery tube 2.

Figure 2:
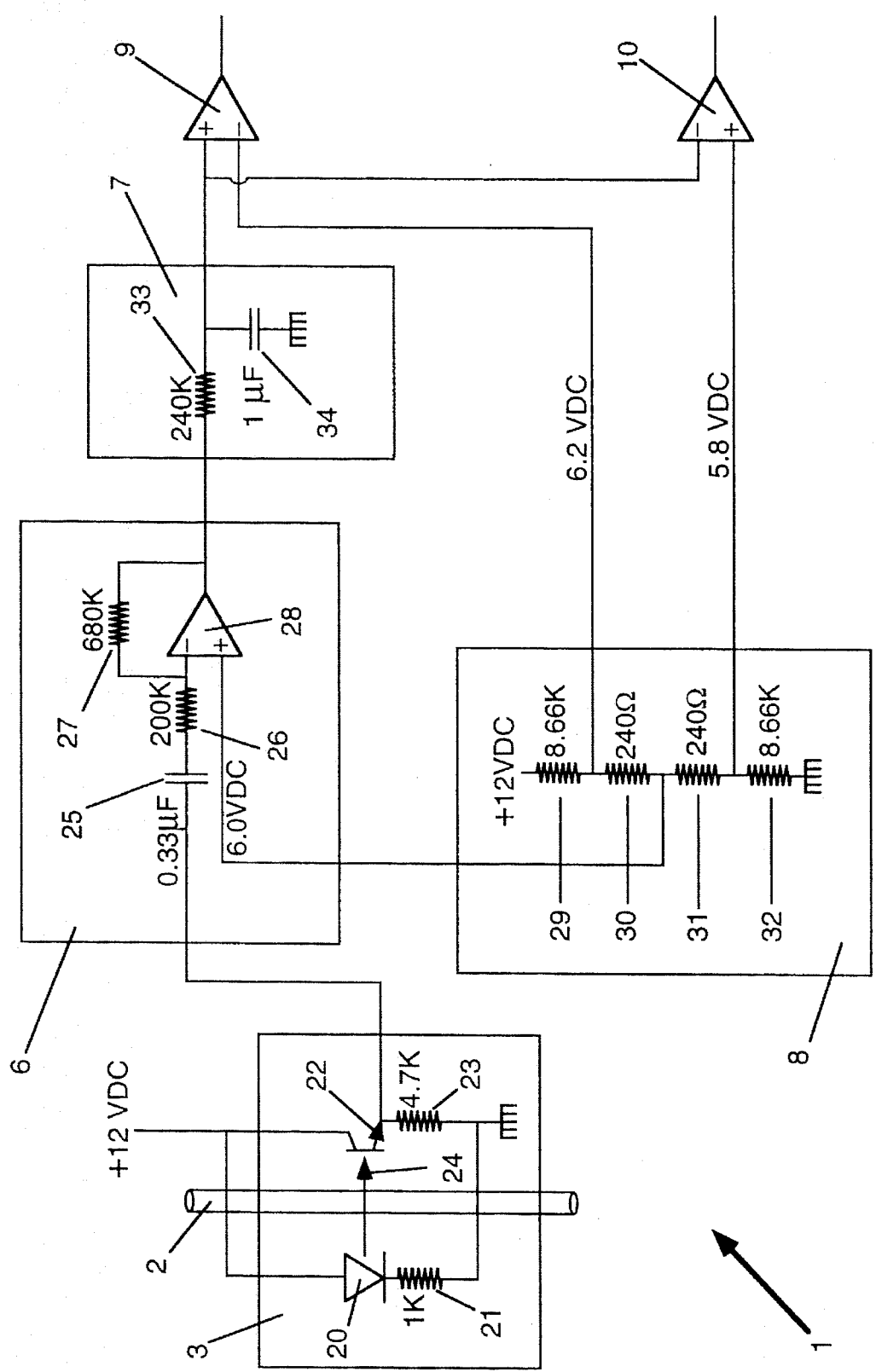
FIG. 2 is a schematic diagram which illustrates one preferred embodiment of circuitry according to the invention of the bubble detector illustrated in FIG. 1.

FIG. 2 is a schematic diagram of the detection head 3, the referencing and drift compensation circuit 6, the integrator 7, the voltage reference 8, and the output amplifiers 9 and 10. The detection head 3 comprises a light emitting diode 20 with its anode connected to a +12 vdc power supply and its cathode connected to a grounded current limiting resistor 21. Detection head 3 also includes a NPN photo transistor 22 with its collector connected to the +12 vdc supply and its emitter connected to a grounded current limiting resistor 23.

Under normal use, the light emitting diode 20 and the photo transistor 22 are positioned on opposite sides of a piece of transparent tubing containing the liquid and gas to be monitored such that light 24 emitted by the light emitting diode 20 passes through the tubing, its contents (liquid and/or gas), and is received by the photo transistor 22. The detected signal output 34 of the detection head 3 is connected to the input of the referencing and drift compensation circuit 6 on one side of decoupling capacitor 25. Circuit 6 consists of a decoupling capacitor 25 which acts to decouple circuit 6 from the absolute output voltage 34 of monitor head 3 and make the circuit reactive only to changes in the output voltage 34 of monitor head 3.

Figure 3A:
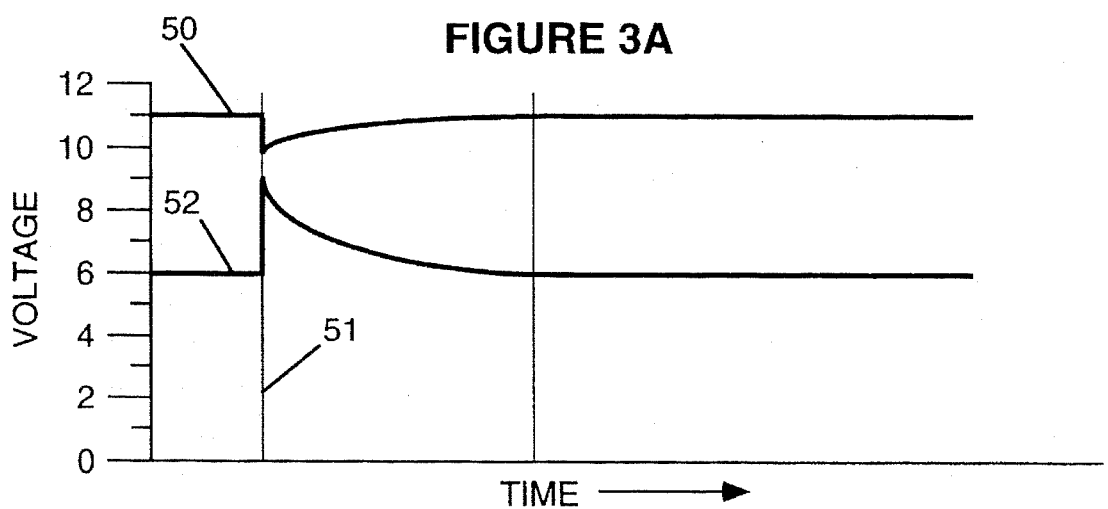
FIGS. 3A–3C illustrate voltage vs. time graphs demonstrating the automatic referencing and drift compensation characteristics of the invention.
Figure 3B:
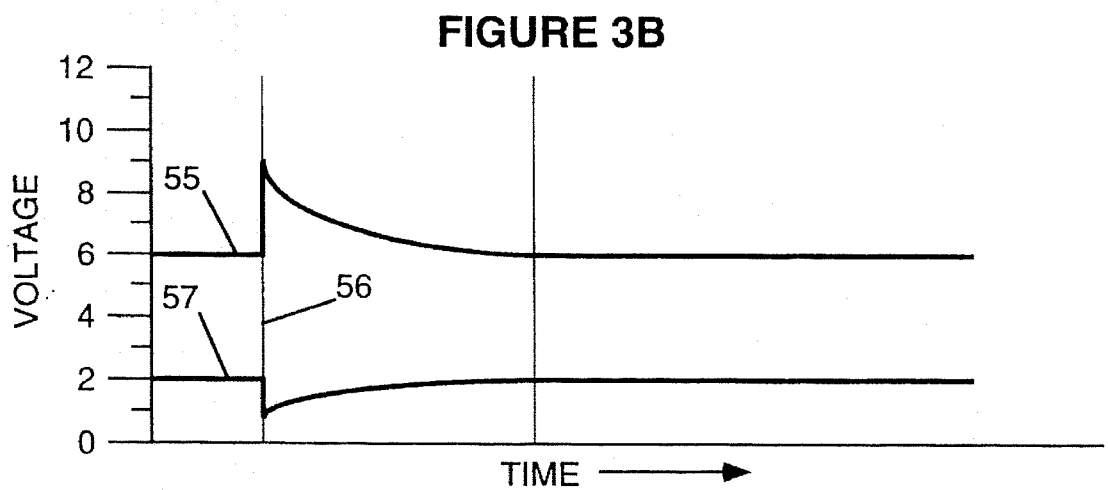

By making circuit 6 responsive only to changes in the output voltage 34 of detector head 3, apparatus 1 eliminates the need for manual referencing typical with prior art bubble detectors. This effect is shown in FIG. 3A and 3B where it can be seen that the output of circuit 6, lines 52 and 55, are identical whether the output 34 from detector head 3 occurs at a high voltage 50 or at a low voltage 57. The only factor affecting the output of circuit 6 is the change in monitor head 3 voltage, not its absolute voltage. The other end of decoupling capacitor 25 is connected to resistor 26 which is connected to the inverting input of amplifier 28. Amplifier 28 has a feedback resistor 27 connected between its output and inverting input and then a 6.0 volt reference connected to its non-inverting input.

Figure 4A:
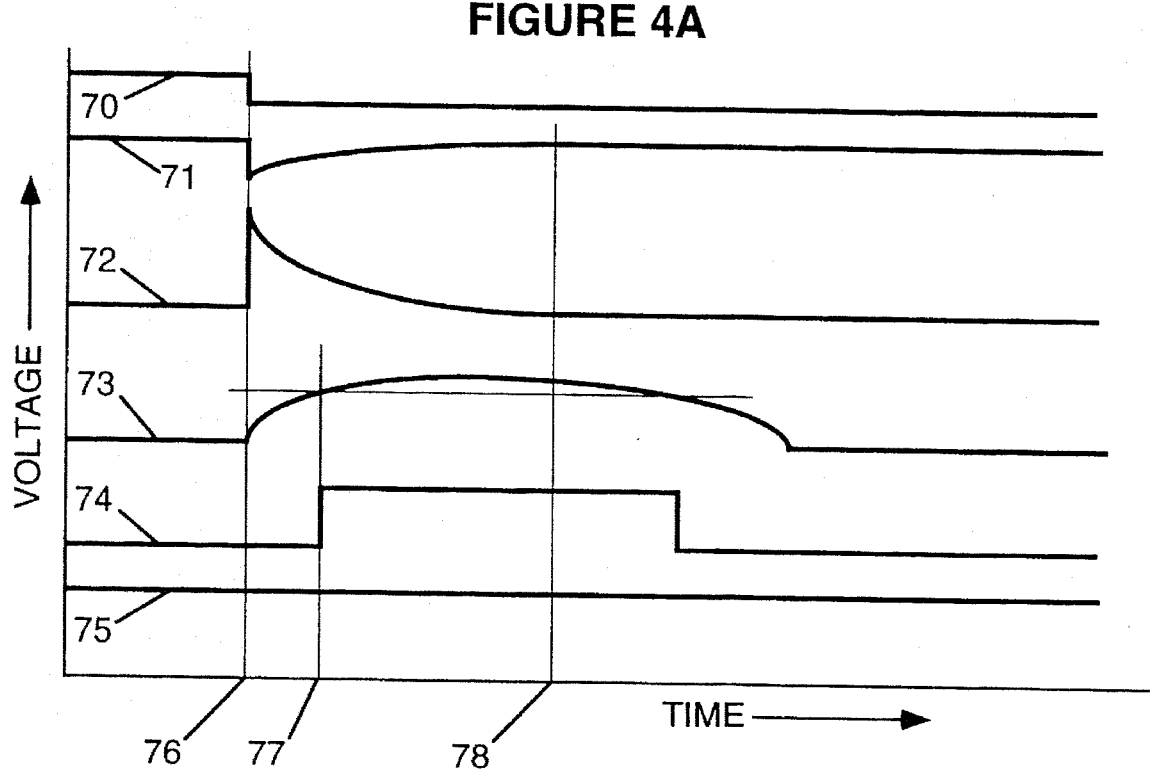
FIGS. 4A and 4B are timing diagrams illustrating the output of the invention according to the schematic diagram illustrated in FIG. 2.

Referencing and drift compensation circuit 6 works as shown in FIG. 4A. When the circuit is at equilibrium (such as during a constant flow of liquid or gas through tubing 2), monitor head 3 applies an arbitrary, but constant, voltage 70 to decoupling capacitor 25. Amplifier 28 has charged or discharged capacitor 25 until the voltage across 25 is such that the voltage at the inverting input of amplifier 28 equals the reference voltage at the non-inverting input. At equilibrium, amplifier 28 has an output voltage of 6.0 volts. If at time 76 a transition from liquid to air occurs in the tubing between diode 20 and transistor 22, the output voltage 70 of monitor head 3 decreases because less light is transmitted through the air and received by transistor 22 than the light transmitted through the liquid and received by the transistor 22. This decrease in voltage 70 causes a voltage 71 to develop across resistor 26 of a proportionate amount. Amplifier 28 responds by increasing its output voltage 72 until capacitor 25 discharges to the point that circuit 6 reestablishes equilibrium at time 78.

Figure 4B:
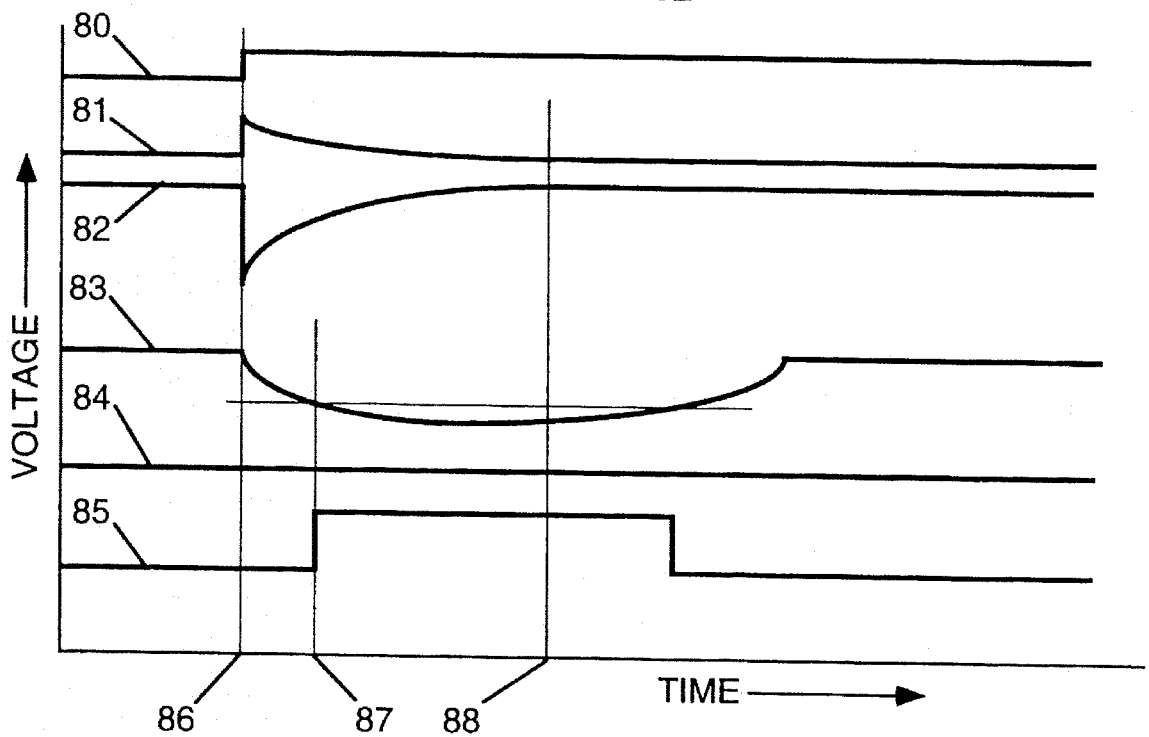

Referring to FIG. 4B, if monitor head 3 senses a transition from air to liquid in the tubing 2 at time 86, the circuit responds identically to the previous example, but in the opposite direction as can be seen from the shape of the voltage curves. Monitor head 3 has the voltage profile shown for curve 80, the voltage across resistor 26 is curve 81 and the output of amplifier 28 is curve 82.

Proportional reference voltages are derived from a voltage divider 8 consisting of resistors 29, 30, 31, and 32 in series. Resistor 29 is connected to the positive power supply then to resistor 30 which is connected to resistor 31 which is connected to resistor 32 which is connected to ground. The junction of 29 and 30 form a 6.2 volt reference, the junction of 30 and 31 form a 6.0 volt reference and the junction of 31 and 32 form a 5.8 volt reference. The output of the referencing and drift compensation circuit 6 is applied to the input of integrator 7. Integrator 7 comprises a resistor 33 in series between the output of amplifier 28 and a grounded capacitor 34. The voltage across capacitor 34 is applied to the non-inverting input of amplifier 9 and to the inverting input of amplifier 10. The inverting input of amplifier 9 is connected to a 6.2 volt reference from voltage divider 8 and the non-inverting input of amplifier 10 is connected to a 5.8 volt reference from voltage divider 8.

Referring to FIG. 4A, it can be seen that the output voltage 73 across capacitor 34 is the integral of the output voltage 72 of amplifier 28. When the output voltage 72 of amplifier 28 increases at time 76, the voltage 73 across capacitor 34 increases with the associated RC time constant of resistor 33 and capacitor 34. If the voltage increase 72 of amplifier 28 is great enough for a sufficient period of time that the voltage 73 across capacitor 34 exceeds 6.2 volts, which occurs at time 77, then the output voltage 74 of amplifier 9 is driven high supplying the signal for a liquid to air transition while the output voltage 75 of amplifier 10 remains unchanged.

Referring to FIG. 4B, when an air to liquid transition is detected by monitor head 3 at time 86, the output voltage 82 of amplifier 28 decreases. If the voltage decrease is great enough for a sufficient period of time that the voltage 83 across capacitor 34 falls below 5.8 volts which occurs at time 87, then the output voltage 85 of amplifier 10 is driven high supplying the signal for a detected air to liquid transition while the output voltage 84 of amplifier 9 remains unchanged.

Figure 3C:
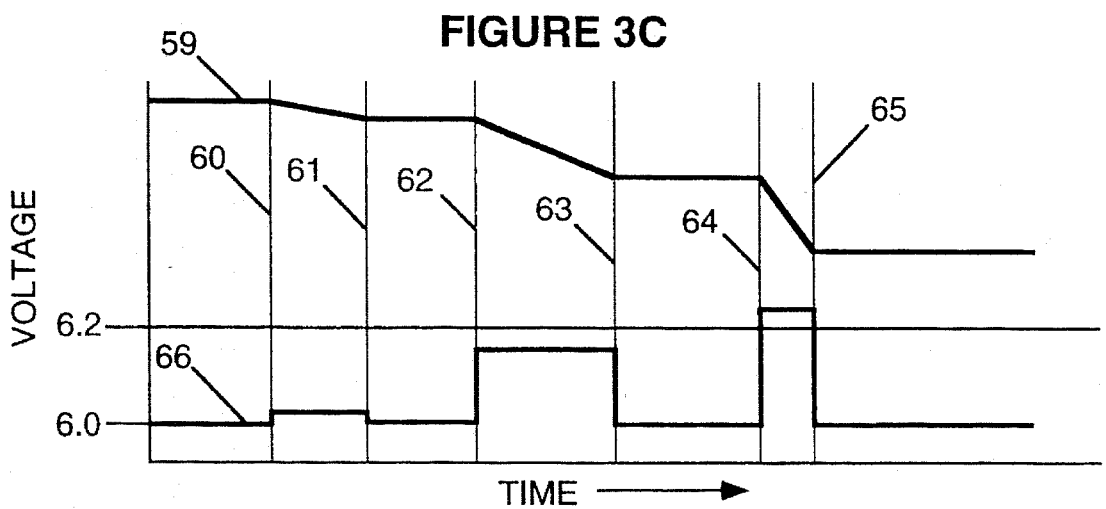

FIG. 3C shows the automatic drift compensation characteristics of automatic referencing and drift compensation circuit 6 for the situation where the output voltage from the detection head 3 decreases with time. The output voltage of detector head 3 decreases (i.e., less light is detected by the receiver) for a number of reasons including change in solvent composition from a solvent that adsorbs less light to a solvent that adsorbs more light, slow decrease in the efficiency of light emitting diode 20, or the efficiency of photo transistor 22. At times 60 and 62 the output voltage 59 of detector head 3 drifts in a negative direction which results in amplifier 28 increasing its output voltage 66 proportionate to the rate of voltage drift. As long as the change in detector voltage 59 decreases at a rate slow enough that the output voltage 66 of amplifier 28 never exceeds the reference voltage at the non-inverting input of amplifier 9, the output voltage of amplifier 9 remains at ground thus generating no alarm signal. At times 61 and 63, when the output voltage of detector head 3 stops changing, the output voltage of amplifier 28 returns to its resting value of 6.0 volts, even though the absolute output voltage 59 of detection head 3 has decreased. The property of circuit 6 to return to its resting voltage of 6.0 volts following a change in the output voltage of the detection head 3 is referred to as automatic drift compensation. At time 64, the output voltage 59 of detection head 3 decreases at a rate great enough that the output voltage 66 of amplifier 28 exceeds the reference voltage at the non-inverting input of amplifier 9. If this condition persists long enough for capacitor 34 to increase its voltage above the reference voltage at the non-inverting input of amplifier 9, then an alarm signal is generated by the output of amplifier 9 in the form of a positive pulse. The action of circuit 6 is identical for the situation where the output voltage of the detector head 3 increases with time, except the change in voltage levels occurs in the opposite direction to those shown in FIG. 3c and for a fast enough rise in voltage, amplifier 10 supplies a positive pulse.

In view of the above, it will be seen that the several objects of the invention are achieved and other advantageous results attained.

As various changes could be made in the above methods without departing from the scope of the invention, it is intended that all matter contained in the above description and shown in the accompanying drawings shall be interpreted as illustrative and not in a limiting sense.

What is claimed is:

1. An apparatus for sensing transitions from liquid to gas or from gas to liquid in a tubing through which the liquid and the gas are flowing, said apparatus comprising:

a transmitter adapted to be adjacent the tubing and generating energy which propagates through the tubing and through the liquid and gas flowing through the tubing;

a receiver associated with the transmitter for detecting the energy transmitted through the liquid and gas flowing through the tubing, said receiver generating a detected signal representative of the transmitted energy;

a drift compensation circuit connected to the receiver, translating the detected signal to a known voltage level and generating a first signal when a transition from liquid air is detected in the tubing and generating a second signal when the transition from air to liquid is detected;

an integrator connected to the drift compensation circuit and integrating the first and second signals; and a detecting circuit connected to the integrator and detecting a direction of change in the polarity of the integrated signal and generating a first alarm signal when the detected direction of change of the integrated signal is positive and a generating a second alarm signal when the detected direction of change of the integrated signal is negative whereby the first alarm signal is representative of either a transition from liquid to gas or a transition from gas to liquid and the second alarm signal is representative of the other transition.

2. The apparatus of claim 1 wherein the drift compensation circuit is connected between the receiver and the integrator for maintaining the detected signal substantially constant relative to the reference.

3. The apparatus of claim 1 wherein the tubing is transparent, wherein the transmitter comprises a light emitting diode on one side of the transparent tubing and wherein the receiver comprises a photodetector opposite to the light emitting diode on the other side of the transparent tubing so that light emitted by the light emitting diode passes through the transparent tubing and the liquid and gas flowing through the transparent tubing.

4. The apparatus of claim 3 wherein the drift compensator circuit is connected between the receiver and the integrator for maintaining the detected signal substantially constant relative to the reference.

5. The apparatus of claim 1 further comprising a referencing circuit connected between the receiver and the integrator for modifying the detected signal relative to a reference, said referencing circuit including a feedback loop connecting the output of the referencing circuit and the detected signal.

6. The apparatus of claim 5 wherein the drift compensation circuit is connected between the receiver and the integrator for maintaining the detected signal substantially constant relative to the reference.

7. The apparatus of claim 5 wherein the tubing is transparent, wherein the transmitter comprises a light emitting diode on one side of the transparent tubing and wherein the receiver comprises a photodetector opposite to the light emitting diode on the other side of the transparent tubing so that light emitted by the light emitting diode passes through the transparent tubing and the liquid and gas flowing through the transparent tubing.

8. The apparatus of claim 1 further comprising a first differential amplifier for comparing the integrated signal to a reference voltage and generating the first alarm signal when the integrated signal increases relative to the reference signal and a second differential amplifier for comparing the integrated signal to a reference voltage and generating a second alarm signal when the integrated signal decreases relative to the reference signal.

9. The apparatus of claim 8 wherein the drift compensation circuit is connected between the receiver and the integrator for maintaining the detected signal substantially constant relative to the voltage reference.

10. The apparatus of claim 9 a referencing circuit connected between the receiver and the integrator for modifying the detected signal relative to the voltage reference.

11. The apparatus of claim 4 wherein the referencing circuit includes a differential amplifier for comparing the detected signal to the voltage reference and having a feedback loop connecting the output of the differential amplifier and the detected signal.

12. The apparatus of claim 8 wherein the tubing is transparent, wherein the transmitter comprises a light emitting diode on one side of the transparent tubing and wherein the receiver comprises a photodetector opposite to the light emitting diode on the other side of the transparent tubing so that light emitted by the light emitting diode passes through the transparent tubing and the liquid and gas flowing through the transparent tubing.

13. The apparatus of claim 8 a referencing circuit connected between the receiver and the integrator for modifying the detected signal relative to the voltage reference.

14. An apparatus for sensing transitions from liquid to gas or from gas to liquid in a transparent tubing through which the liquid and the gas are flowing, said apparatus comprising:

a transmitter adapted to be adjacent the tubing and generating energy which propagates through the tubing and through the liquid and gas flowing through the tubing;

a receiver associated with the transmitter for detecting the energy transmitted through the liquid and gas flowing through the tubing, said receiver generating a detected signal representative of the transmitted energy;

a referencing and drift compensating circuit for modifying the detected signal relative to a reference voltage; and a detecting circuit detecting a change in magnitude of the modified detected signal and generating an alarm signal when the modified detected signal changes in magnitude relative to the reference voltage whereby the alarm signal is representative of either a transition from liquid to gas or a transition from gas to liquid.

15. The apparatus of claim 14 wherein the referencing and drift compensating circuit comprises a capacitor decoupling the level of the detected signal from the level of the reference signal, a differential amplifier comparing the decoupled detected signal to the voltage reference and a feedback loop connecting the output of the differential amplifier and the detected signal.

16. An apparatus for sensing transitions from liquid to gas or from gas to liquid in tubing through which the liquid and the gas are flowing, said apparatus comprising:

a light emitting diode adapted to be adjacent the tubing and generating light which propagates through the tubing and through the liquid and gas flowing through the tubing;

a photosensitive detector associated with the diode for detecting the light transmitted through the tubing and through the liquid and gas flowing through the tubing, said detector generating a detected signal representative of the transmitted light; and a first differential amplifier circuit comparing the detected signal to a first reference voltage and providing a output signal, said-output signal increases in magnitude when the detected signal increases relative to the first reference voltage and said output signal decreases in magnitude when the detected signal decreases relative to the first reference voltage.

17. The apparatus of claim 16 further comprising a reference circuit generating the first reference voltage and generating a second reference voltage proportional to the first reference voltage and a third reference voltage proportional to the first reference voltage, a second differential amplifier for comparing the output signal to the second reference voltage and providing a first alarm signal and a third differential amplifier for comparing the output signal to the third reference voltage and providing a second alarm signal whereby the first alarm signal is representative of one of either a transition from liquid to gas or a transition from gas to liquid and the second alarm signal is representative of the other transition.

18. The apparatus of claim 17 wherein the second reference voltage is greater than the first reference voltage and the third reference voltage is less than the first reference voltage.

19. The apparatus of claim 18 further comprising an integrator integrating the output signal, said integrator between the first differential amplifier and the second and third differential amplifiers so that the second and third differential amplifiers compare the integrated output signal to the second and third references, respectively.

20. A method for sensing transitions from liquid to gas or from gas to liquid in tubing through which the liquid and the gas are flowing, said method comprising the steps of:

generating light which propagates through the tubing and through the liquid and gas flowing through the tubing;

detecting the light transmitted through the tubing and through the liquid and gas flowing through the tubing;

generating a detected signal representative of the transmitted light; and comparing a direction of change of the detected signal to a first reference voltage and providing an output signal, said output signal increases in magnitude when the detected signal increases relative to the first reference voltage and said output signal decreases in magnitude when the detected signal decreases relative to the first reference voltage.

* * * * *